United States Patent [19]

Ornath et al.

[11] Patent Number: 5,942,699
[45] Date of Patent: Aug. 24, 1999

[54] METHOD AND APPARATUS FOR SAMPLING CONTAMINANTS

[75] Inventors: Fredy Ornath, Tel Aviv; Sam S. Buechler, Holon, both of Israel

[73] Assignee: R.A.Y. Buechler Ltd., Tel Aviv, Israel

[21] Appl. No.: 08/873,394

[22] Filed: Jun. 12, 1997

[51] Int. Cl.[6] .................................................. G01N 1/24
[52] U.S. Cl. ............................. 73/863.21; 73/863.12; 73/863.23; 73/864.33
[58] Field of Search ..................... 73/863.11, 863.12, 73/863.21, 863.23, 863.31, 863.33, 864.33, 864.34, 864.35

[56] References Cited

U.S. PATENT DOCUMENTS

| | | |
|---|---|---|
| 3,709,026 | 1/1973 | Rhodes et al. .................. 73/12.11 |
| 3,866,474 | 2/1975 | Hasselmann ..................... 141/67 X |
| 3,942,357 | 3/1976 | Jenkins . | |
| 3,998,101 | 12/1976 | Bradshaw et al. . | |
| 4,024,217 | 5/1977 | Wexler et al. ................ 250/288 X |
| 4,045,997 | 9/1977 | Showalter et al. . | |
| 4,202,200 | 5/1980 | Ellson . | |
| 4,580,440 | 4/1986 | Reid et al. ...................... 73/864 X |
| 4,718,268 | 1/1988 | Reid et al. ...................... 73/864 X |
| 4,964,309 | 10/1990 | Jenkins ............................. 73/864.81 |
| 5,092,155 | 3/1992 | Rounbehler et al. ............ 73/167 X |
| 5,092,218 | 3/1992 | Fine et al. ........................... 86/50 |
| 5,092,220 | 3/1992 | Rounbehler ....................... 89/1.1 |
| 5,138,889 | 8/1992 | Conrad ............................. 73/863.12 |
| 5,162,652 | 11/1992 | Cohen et al. ...................... 250/288 |
| 5,174,149 | 12/1992 | Grob et al. ........................ 73/23.41 |
| 5,317,930 | 6/1994 | Wedding ....................... 73/863.23 X |
| 5,345,809 | 9/1994 | Corrigan et al. .................... 73/23.2 |
| 5,400,665 | 3/1995 | Zhu et al. ......................... 73/863.12 |
| 5,476,794 | 12/1995 | O'Brien et al. ...................... 436/92 |
| 5,585,575 | 12/1996 | Corrigan et al. ................ 73/863.71 |

OTHER PUBLICATIONS

*Patent Abstracts of Japan* Grp C0800, vol. 15, No. 38 Abs Pub Date Jan. 30, 1991 (02–274868) "Producing Device for Semiconductor" Minoru Inoue.

*Primary Examiner*—Thomas P. Noland
*Attorney, Agent, or Firm*—Mark M. Friedman

[57] ABSTRACT

A method for collectively sampling a plurality of cargo items for contaminants such as chemical residues. The items are placed in a generally airtight chamber and agitated physically to release particulates and vapors from the surfaces and interior of the items. The methods of physical agitation include vibrating the items, and pressurizing and depressurizing the chamber, with the pressurizing being done by introducing bursts of high pressure air into the chamber and by directing jets of high pressure air at the cargo. Optionally, the high pressure air may be heated or mixed with solvent vapors. This physical agitation drives particulates and vapors of contaminants into suspension in the air in the chamber. Air withdrawn during depressurization is passed through a collection system to collect the particulates and vapors for subsequent analysis.

27 Claims, 3 Drawing Sheets

5,942,699

METHOD AND APPARATUS FOR SAMPLING CONTAMINANTS

FIELD AND BACKGROUND OF THE INVENTION

The present invention relates to a method and apparatus for sampling cargo for chemical residues and, more particularly, to a method and apparatus for extracting particulates and vapors of chemical residues simultaneously from multiple cargo items.

Cargo, such as agricultural produce, general merchandise, and passengers' baggage, is routinely checked for chemical residues at transit points such as airports, seaports and border crossings generally. In the case of agricultural produce, the residues sought generally are pesticides and other health hazards. In the case of general merchandise and baggage, the residues sought include illicit substances such as drugs and explosives. This sampling can be tedious and time-consuming. For example, agricultural produce is inspected by selecting a representative sample, mechanically chopping the sample and chemically analyzing the sample. The familiar x-ray inspection of passengers' baggage at airports is performed one item at a time. The quality of this inspection depends on the alertness of the operator to spot suspicious items by their outline against complex backgrounds, as well as on equipment limitations. For a more intensive search based on chemical analysis, chemical samples are collected manually from the outside surfaces, or less commonly from the surfaces of the inside contents, of suspect baggage and parcels and transferred to an analytical instrument or to a reagent chemical test kit for identification. These manual sampling/analysis procedures can detect traces of pesticides on or within agricultural produce, as well as traces of illegal drugs and explosives deposited on the sampled surfaces in the course of handling drugs and explosives and hiding them in the baggage, parcels or cargo, but these procedures generally are slow and tedious, and therefore are restricted to a limited random sample of the inspected items.

A variety of automatic and semiautomatic systems have been proposed for collecting vapors and particulates from cargo items. These generally require that the items be loaded individually into a sampling chamber, although Cohen et al., in U.S. Pat. No. 5,162,652, teach the simultaneous loading of several items into several chambers, albeit still only one item per chamber. The invention of Cohen et al. and also the inventions of Jenkins, described in U.S. Pat. No. 3,941,357, and of Bradshaw et al., described in U.S. Pat. No. 3,998,101, are directed towards extracting vapor from the interior of sealed cargo by varying the pressure within the sampling chamber, typically by up to about 10% on either side of atmospheric pressure. Corrigan et al., in U.S. Pat. No. 5,345,809, and Reid et al., in U.S. Pat. No. 4,580,440, address the problem of sampling particulates on the surfaces of cargo items. Corrigan et al. teach a sampling chamber in which brushes remove particulates from the surfaces of cargo items. Reid et al. teach the agitation of a cargo transport container to suspend, in the air therein, particulates from the surfaces of the cargo items therein, followed by the sampling of the air with the suspended particulates. None of these prior art patents has addressed the problem of sampling particulates contained inside the cargo items.

There is thus a widely recognized need for, and it would be highly advantageous to have, an automatic contaminant sampling method that extracts samples automatically from several inspected items such as cargo items at once, and also extracts particulate contaminants from the interiors of the inspected items.

SUMMARY OF THE INVENTION

According to the present invention there is provided a method for sampling surfaces and interiors of a plurality of items for contaminant particulates and contaminant vapors, including the steps of: (a) sealing the items inside a chamber containing air at a certain pressure; (b) agitating the items, thereby releasing the particulates and the vapors from the surfaces and the interiors of the items into the air; and (c) inducing a flow of the air, together with the released particulates and vapors, towards a collection system.

According to the present invention there is provided a method for sampling surfaces and interiors of a plurality of items for contaminant particulates and contaminant vapors of chemical residues, including the steps of: (a) sealing the items inside a chamber; (b) introducing a gas into the chamber at a certain pressure; (c) agitating the items, thereby releasing the particulates and the vapors from the surfaces and the interiors of the items into the gas; and (d) inducing a flow of the gas, together with the released particles and vapors, towards a collection system.

According to the present invention there is provided an apparatus for sampling cargo for particulates and vapors of chemical residues, including: (a) a chamber, enclosing a gas at a certain pressure, wherein the cargo is placed for sampling; (b) a mechanism for agitating the cargo, thereby releasing the particulates and vapors into the gas; (c) a collection system for removing the particulates and vapors from the gas; and (d) a mechanism for inducing a flow of the gas, together with the particulates and vapors, towards the collection system.

According to the present invention, cargo items on a pallet are loaded en masse into an airtight chamber and subjected to physical agitation, including vibration, blasts of pressurized air into the chamber, jets of pressurized air directed at the cargo, and cycles of pressurization and depressurization, to release both vapors and particulates from both the interiors and the outer surfaces of the cargo items. The pressurized air may be heated before being directed at the cargo items. Solvent vapors may be introduced to the pressurized air, before it is directed at the cargo items. The adsorption of solvents on the surfaces of particulates often decreases the attractive forces between particulates adsorbed on surfaces and the surfaces on which they are adsorbed, making the particulates easier to dislodge. In addition, most solvents have a higher molecular mass than the constituents of air. Adding these solvents to the air increases the average momentum transfer in a collision between the air and the surfaces on which the particles are adsorbed. Typical solvents used for this purpose include carbon dioxide, acetone, dimethyl sulfoxide, propanol and organic amides. The object of this physical agitation is to knock loose aerosol-size contaminant particles on the exterior and interior surfaces of the items, and to encourage the vaporization of low vapor pressure chemical residues into the air in the chamber. In this manner, contaminant particulates from the outer surfaces of the items and from the interiors of the items are placed in suspension in the air in the chamber, and contaminant vapors from the outer surfaces of the items and from the interiors of the items are mixed with the air in the chamber. During the depressurization phases, air withdrawn from the chamber is passed through a collection system to collect the vapors and particulates. The collected vapors and particulates then are transferred to conventional analytic instruments for identification. If a targeted substance such as a pesticide residue, a trace of an explosive, or a trace of an illegal drug, is identified during this analysis, appropriate steps may be taken, including generating an audible and visible alarm. In addition, the items that were sampled collectively now may be sampled individually, using one or more of the prior art methods, to identify the item bearing the source of the targeted substance. In an airport setting, where the overwhelming majority of the baggage items do not contain contraband, the present invention may be used for an efficient mass preliminary screening of baggage items which is much faster than the prior art methods that deal with one baggage item at a time.

To keep the particulates in suspension during the depressurization phases, it has been found necessary to continue the blasts of pressurized air into the chamber during the depressurization phase. These blasts are directed towards the collection system, thereby supplementing the suction that effects the depressurization in inducing a flow of air that entrains the particulates and transports them to the collection system. There are prior art systems, such as those taught by Corrigan et al. in the U.S. Pat. No. 5,345,809 cited above, and by Ellson in U.S. Pat. No. 4,202,200, in which continuously flowing air is used to collect vapors and particulates from people transiting a walk-through sampling chamber and transport the vapors and particulates to a collection system, but there are no prior art systems in which intermittent blasts of air is used to direct the flow of suspended particulates towards a collection system.

At the end of a session of physical agitation, the pallet bearing the cargo items is removed from the chamber, and another pallet-load of cargo items is placed in the chamber for sampling. In this way, the cargo is sampled nondestructively and collectively, allowing the cargo to be sampled for contaminants much more quickly and thoroughly than by the present art methods.

In one aspect of the present invention, the air in the chamber is replaced with a carrier gas such as carbon dioxide. The cargo then is subjected to physical agitation as described above, with the carrier gas being substituted for air. In other words, the cargo is subjected to pressurized blasts and jets of carrier gas, and the pressure of the carrier gas within the chamber is cycled up and down, with carrier gas containing chemical residue vapors and suspended particulates being withdrawn for collection during the depressurization phases.

Although the present invention is directed primarily towards the collection of chemical residues, such as traces of explosives, drugs and pesticides, in the form of particulates and vapors, the scope of the present invention includes the collection of contaminants in general, including particulate contaminants not commonly considered "chemical" residues, such as bacteria and viruses.

BRIEF DESCRIPTION OF THE DRAWINGS

The invention is herein described, by way of example only, with reference to the accompanying drawings, wherein:

FIG. 1 is a schematic axial cross section through a sampling chamber of the present invention;

FIG. 2 is a schematic transverse cross section through the sampling chamber of FIG. 1;

FIG. 3 is a partial schematic cross section of a collection system.

DESCRIPTION OF THE PREFERRED EMBODIMENTS

The present invention is of a method and apparatus which can be used to sample a plurality of cargo items collectively for contaminants. Specifically, the present invention can be used to sample both the surfaces and the exteriors of cargo items for contaminants in the forms of particulates and vapors collectively, nondestructively, and rapidly.

The principles and operation of contaminant sampling according to the present invention may be better understood with reference to the drawings and the accompanying description.

Referring now to the drawings, FIG. 1 is a schematic axial cross section through a sampling chamber 10 of the present invention, and FIG. 2 is a schematic transverse cross section through chamber 10. Within chamber 10 is a table 20 mounted on springs 22. Below table 20 is a mechanism for oscillating table 20. The specific illustrative mechanism shown here includes a vertical partition 24, rigidly attached to the bottom of table 20, to which are attached two contrarotating unbalanced motors 26. One example of an unbalanced motor 26 that is suitable for this application is the I. F. E. Model G75T, manufactured by Industrie Einrichtungen Fertigungs of Weindhofen an der Ybbs, Austria. Leading into chamber 10 from the top and one side thereof respectively, are pressure conduits 40 and 40' for conducting pressurized air into chamber 10. The air in conduits 40 and 40' is pressurized by a compressor 48. Conduits 40 and 40' are terminated by valves 42 and 42'. Conduit 40 branches into a pair of conduits 41 that in turn lead through a pair of heaters 44, wherein the pressurized air conveyed therethrough from compressor 48 may be heated to up to about 250° C., and through a pair of misting devices 46 that introduces vapors of a solvent into the pressurized air conveyed therethrough from compressor 48. Similarly, conduit 40' leads through a heater 44' that is similar to heaters 44, and through a misting device 46' that is similar to misting device 46. Valve 42' opens directly into chamber 10, so that pressurized air introduced into chamber 10 in bursts, as described below, expands into chamber 10 in substantially hemispherical pressure to waves. Valves 42 open into nozzles 43 that forms pressurize air entering chamber 10 therethrough into high pressure jets. Preferably, valves 42 and 42' are fast-acting, with a response time no greater than about 30 milliseconds.

On the side of chamber 10 opposite valve 42' is a depressure conduit 54. A vacuum pump 50 withdraws air from chamber 10 via conduit 54. Air withdrawn via conduit 54 traverses a collection system 52 that removes vapors and aerosol particles of possible contaminants from the air passing therethrough. Note the positioning of depressure conduit 54 opposite valve 42'. This positioning enables the blasts of air from valve 42' to induce a flow of air towards depressure conduit 54 that, in addition to keeping the particulates in suspension, entrains the particulates and transports them to depressure conduit 54. For simplicity, only one each of conduits 40, 40' and 54, and only two of conduits 41, are shown in the Figures. Practical sampling chambers 10 preferably include up to 16 of conduits 40, 40' or 41, and up to 8 of conduits 54.

Compressors suitable for use as compressor 48 include the type LF-5S manufactured by Atlas Copco Airpower of Wilrijk, Belgium. Pumps suitable for use as vacuum pump 50 include the type 5MVP manufactured by Ahim Polak of Azor, Israel. Valves suitable for use as valves 42 and 42' include the type CA76T020 3" valve manufactured by Goyen Controls of Sidney, Australia.

Chamber 10 also is provided with two airtight doors 12 and 12' at either end of chamber 10. Doors 12 and 12' are raised automatically to open chamber 10 and lowered to close and seal chamber 10.

To sample cargo for chemical residues, door 12 is raised if necessary to open chamber 10, and a pallet 72 bearing cargo items 70 is deposited on table 20 by a loading mechanism such as a forklift 74. Door 12 is lowered, and door 12' is lowered if necessary, thereby sealing chamber 10. Cargo items 70 then are subjected to four kinds of physical agitation:

A. Motors 26 oscillate table 20, thereby vibrating cargo items 70. The preferred range of vibration frequencies is between about 0.5 cycles per second and about 20 cycles per second.

B. The air pressure within chamber 10 is cycled between a maximum of about 1.5 atmospheres and a minimum of about 0.5 atmospheres. The pressurization phase of each cycle is effected by pumping air into chamber 10 via conduits 40 and 40'. The depressurization phase of each cycle is effected by pumping air out of chamber 10 via conduit 54. Preferably, the pressure is cycled at a frequency of between about 0.2 cycles per minute and about 2 cycles per minute, so that every pressurization-depressurization cycle lasts between about 30 seconds and about 5 minutes. Note that the placement of conduits 40' and 54 on opposite sides of chamber 10 tends to promote unidirectional air flow through chamber 10.

C. The pressurization of chamber 10 is not gradual, but is effected in jets of high-pressure air from conduits 41 via nozzle 43 that are directed at cargo items 70, and in bursts of high-pressure air from conduit 40' into chamber 10 generally. The frequency of the jets is between about one jet per second and about 6 jets per second, and is achieved by opening and closing valve 42' between about once per second and about 6 times per second. The frequency of the bursts is between about one burst every 10 seconds and about 5 bursts per second, and is achieved by opening and closing valves 42 between about once every 10 seconds and about 5 times per second. The jets are active only during the pressurization phases. The bursts continue into the depressurization phases, for almost the entire duration of the depressurization phases, to keep the particulates suspended in the air and to help induce a flow of air directed towards conduit 54.

D. The high pressure air introduced to chamber 10 via conduit 40 is heated by heaters 44 and 44' to about 250° C. To shorten the heating time and provide additional convectional circulation, the air already within the chamber also is heated by one or more heaters (not shown) located inside the chamber.

The effect of this physical agitation is to drive vapors and particulates from the surfaces and interior of cargo items 70 into suspension in the air in chamber 10. During the depressurization phases of the pressurization/depressurization cycles, some of this air is drawn through collection system 52. Any one of a variety of collection systems, including impact concentrators and cyclone concentrators, may be used. FIG. 3 is a partial schematic cross section of one illustrative collection system 52, an impact concentrator. Air exiting chamber 10 via conduit 54 is accelerated by passing through a constriction 56 and impacts on a removable collection medium 58 to which the particles entrained in the air flow adhere. Preferably, collection medium 58 is a filter, for example fluorocarbon fiber filter paper having a pore size of about 30 microns. Part of the air flow, including vapors, passes through the filter into an exit conduit 60'. The rest of the air flow exits collection system 52 via an exit conduit 60 to a cold trap (not shown) where the vapors are collected. Alternatively, or additionally, collection medium 58 may include strips of a material such as polyimide film that adsorbs the vapors.

The particulates and vapors collected in collection system 52 are analyzed by commercially available analytical instruments. Devices suitable for performing explosive detection analyses include the "EGIS" high speed gas chromatography and chemical luminescence explosive detection instrument, developed and manufactured by Thermedics Detection Inc. of Woburn Mass. and partially described in their U.S. Pat. No. 5,092,155.

The physical agitation described above is continued for between about one minute and about 4 minutes. Then chamber 10 is brought to atmospheric pressure, door 12' is opened and an unloading mechanism such as forklift 74' is used to remove pallet 72 and cargo items 70 thereon from chamber 10.

While the invention has been described with respect to a limited number of embodiments, it will be appreciated that many variations, modifications and other applications of the invention may be made.

What is claimed is:

1. A method for sampling surfaces and interiors of a plurality of items for contaminant particulates and contaminant vapors, comprising the steps of:
   (a) sealing the items inside a chamber containing air;
   (b) vibrating the items directly, thereby releasing the particulates and the vapors from the surfaces and the interiors of the items into said air; and
   (c) inducing a flow of said air, together with the released particulates and vapors, towards a collection system, by introducing bursts of said air into said chamber.

2. The method of claim 1, wherein said vibrating is effected at a frequency between about 0.5 cycles per second and about 20 cycles per second.

3. The method of claim 1, wherein said bursts are introduced into said chamber at a frequency between about one burst per 10 seconds and about 5 bursts per second.

4. The method of claim 3, wherein said air is heated to a temperature of up to about 250° C. before being introduced to said chamber in said bursts.

5. The method of claim 1, further comprising the step of:
   (d) collecting the particulates and the vapors from said air, in said collection system.

6. The method of claim 5, wherein said collecting of the particulates and the vapors includes separating the particulates from the vapors.

7. The method of claim 6, wherein the particulates are collected on fluorocarbon fiber filter paper.

8. The method of claim 7, wherein said fluorocarbon fiber filter paper has pores of a diameter of about 30 microns.

9. The method of claim 1, wherein said vibrating of the items and said inducing of said flow are effected substantially simultaneously.

10. An apparatus for sampling cargo for particulates and vapors of chemical residues, comprising:
   (a) a chamber, enclosing a gas at a certain pressure, wherein the cargo is placed for sampling;
   (b) a mechanism for directly vibrating the cargo, thereby releasing the particulates and vapors into said gas, said mechanism for directly vibrating the cargo including:
      (i) a table, within said chamber, whereon the cargo is placed for sampling, and
      (ii) a mechanism for vibrating said table;
   (c) a collection system for removing the particulates and vapors from said gas; and (d) a mechanism for inducing a flow of said gas, together with said particulates and vapors, towards said collection system.

11. The apparatus of claim 10, wherein said gas is air.

12. The apparatus of claim 10, wherein said collection system includes a mechanism for separating the particulates and the vapor from said gas and from each other.

13. The apparatus of claim 10, wherein said mechanism for inducing said flow of said gas towards said collection system includes a mechanism for introducing said gas into said chamber in bursts.

14. A method for sampling surfaces and interiors of a plurality of items for contaminant particulates and contaminant vapors, comprising the steps of:
   (a) sealing the items inside a chamber containing air;
   (b) agitating the items by introducing heated bursts of said air into said chamber, thereby releasing the particulates and the vapors from the surfaces and the interiors of the items into said air; and
   (c) inducing a flow of said air, together with the released particulates and vapors, towards a collection system.

15. The method of claim 14, wherein said bursts are introduced into said chamber at a frequency between about one burst per 10 seconds and about 5 bursts per second.

16. The method of claim 14, wherein said air is heated to a temperature of up to about 250° C. before being introduced to said chamber in said bursts.

17. A method for sampling surfaces and interiors of a plurality of items for contaminant particulates and contaminant vapors, comprising the steps of:
   (a) sealing the items inside a chamber containing air;
   (b) agitating the items by directing jets of said air at the items, thereby releasing the particulates and the vapors from the surfaces and the interiors of the items into said air; and
   (c) inducing a flow of said air, together with the released particulates and vapors, towards a collection system.

18. The method of claim 17, wherein said jets of said air are directed at the items at a frequency between about once per second and about 6 times per second.

19. The method of claim 17, wherein a solvent is introduced to said air.

20. The method of claim 19, wherein said solvent is selected from the group consisting of carbon dioxide, acetone, dimethyl sulfoxide, propanol and organic amides.

21. The method of claim 17, wherein said air is heated to a temperature of up to about 250° C. before being directed at the items in said jets.

22. An apparatus for sampling cargo for particulates and vapors of chemical residues, comprising:
   (a) a chamber, enclosing a gas at a certain pressure, wherein the cargo is placed for sampling;
   (b) a mechanism for heating a portion of said gas and introducing said heated gas into said chamber in bursts, thereby releasing the particulates and vapors into said gas;
   (c) a collection system for removing the particulates and vapors from said gas; and
   (d) a mechanism for inducing a flow of said gas, together with said particulates and vapors, towards said collection system.

23. An apparatus for sampling cargo for particulates and vapors of chemical residues, comprising:
   (a) a chamber, enclosing a gas at a certain pressure, wherein the cargo is placed for sampling;
   (b) a mechanism for directing jets of said gas at the cargo, thereby releasing the particulates and vapors into said gas;
   (c) a collection system for removing the particulates and vapors from said gas; and
   (d) a mechanism for inducing a flow of said gas, together with said particulates and vapors, towards said collection system.

24. The apparatus of claim 23, wherein said mechanism for directing jets of said gas at the cargo includes a mechanism for heating said gas.

25. An apparatus for sampling cargo for particulates and vapors of chemical residues, comprising:
   (a) a chamber, enclosing a gas at a certain pressure, wherein the cargo is placed for sampling;
   (b) a mechanism for agitating the cargo, thereby releasing the particulates and vapors into said gas, said mechanism for agitating the cargo including:
      (i) a table, within said chamber, whereon the cargo is placed for sampling, and
      (ii) a mechanism for vibrating said table;
   (c) a collection system for removing the particulates and vapors from said gas; and
   (d) a mechanism for inducing a flow of said gas, together with said particulates and vapors, towards said collection system.

26. An apparatus for sampling cargo for particulates and vapors of chemical residues, comprising:
   (a) a chamber, enclosing a gas at a certain pressure, wherein the cargo is placed for sampling;
   (b) a mechanism for directly vibrating the cargo, thereby releasing the particulates and vapors into said gas;
   (c) a collection system for removing the particulates and vapors from said gas; and
   (d) a mechanism for inducing a flow of said gas, together with said particulates and vapors, towards said collection system, said mechanism for inducing said flow of said gas towards said collection system including a mechanism for introducing said gas into said chamber in bursts.

27. The apparatus of claim 26, wherein said mechanism for introducing said gas into said chamber in bursts includes a mechanism for heating said gas.

* * * * *

(12) EX PARTE REEXAMINATION CERTIFICATE (8179th)
United States Patent
Ornath et al.

(10) Number: US 5,942,699 C1
(45) Certificate Issued: Apr. 26, 2011

(54) METHOD AND APPARATUS FOR SAMPLING CONTAMINANTS

(75) Inventors: Fredy Ornath, Tel Aviv (IL); Sam S. Buechler, Holon (IL)

(73) Assignee: Ray Buechler Holdings (1995) Ltd. (IR)

Reexamination Request:
No. 90/006,877, Nov. 26, 2003

Reexamination Certificate for:
| | |
|---|---|
| Patent No.: | 5,942,699 |
| Issued: | Aug. 24, 1999 |
| Appl. No.: | 08/873,394 |
| Filed: | Jun. 12, 1997 |

(51) Int. Cl.
*G01N 1/24* (2006.01)

(52) U.S. Cl. .............. 73/863.21; 73/863.12; 73/863.23; 73/864.33

(58) Field of Classification Search .............. 73/863.11, 73/863.12, 863.21, 863.23, 863.31, 863.33, 73/864.33, 864.34, 864.35
See application file for complete search history.

(56) References Cited

U.S. PATENT DOCUMENTS

| | | | |
|---|---|---|---|
| 3,985,017 A | * 10/1976 | Goldsmith | ............ 436/116 |
| 3,998,101 A | 12/1976 | Bradshaw et al. | |
| 4,422,334 A | 12/1983 | Yasuda | |
| 4,483,261 A | 11/1984 | Green et al. | |
| 4,718,268 A | 1/1988 | Reid et al. | |
| 4,877,433 A | * 10/1989 | Oshitari | ............ 55/486 |
| 4,896,547 A | 1/1990 | Arney et al. | |
| 4,909,090 A | 3/1990 | McGown et al. | |
| 5,092,218 A | 3/1992 | Fine et al. | |
| 5,202,023 A | 4/1993 | Trimmer et al. | |
| 5,642,393 A | 6/1997 | Krug et al. | |

OTHER PUBLICATIONS

Otani, Y. et al.; "Removal of Fine Particles From Smooth Flat Surfaces by Consecutive Pulse Air Jets;" Aerosol Science Technology; vol. 23; 1995; pp. 665–673.
Otani, Y. et al.; "Removal of Fine Particles From Wafer Surface by Pulse Air Jets;" Kagaku Kogaku Ronbunshu; (1993) 19; pp. 114–119.
Masuda, H. et al.; "The Removal of Particles From Flat Surfaces Using a High–Speed Air Jet;", Advanced Powder Technology; vol. 5; No. 2; 1994; pp. 205–217.
Gotoh, K. et al.; "High-Efficiency Removal of Fine Particles Deposited on a Solid Surface;" J. Soc Powder Tech Jpn; vol. 31; No. 10; 1994; pp. 726–733.
Liu, B. Y. H. et al.; "Development of Particle Standards for Testing Explosive Detection Systems: Characterization of the Adhesion Forces Between Composition 4 Particles and Polyethylene;" SPIE Cargo Inspection Technologies; vol. 2276; 1994; pp. 45–55.

* cited by examiner

*Primary Examiner*—Joseph A. Kaufman

(57) ABSTRACT

A method for collectively sampling a plurality of cargo items for contaminants such as chemical residues. The items are placed in a generally airtight chamber and agitated physically to release particulates and vapors from the surfaces and interior of the items. The methods of physical agitation include vibrating the items, and pressurizing and depressurizing the chamber, with the pressurizing being done by introducing bursts of high pressure air into the chamber and by directing jets of high pressure air at the cargo. Optionally, the high pressure air may be heated or mixed with solvent vapors. This physical agitation drives particulates and vapors of contaminants into suspension in the air in the chamber. Air withdrawn during depressurization is passed through a collection system to collect the particulates and vapors for subsequent analysis.

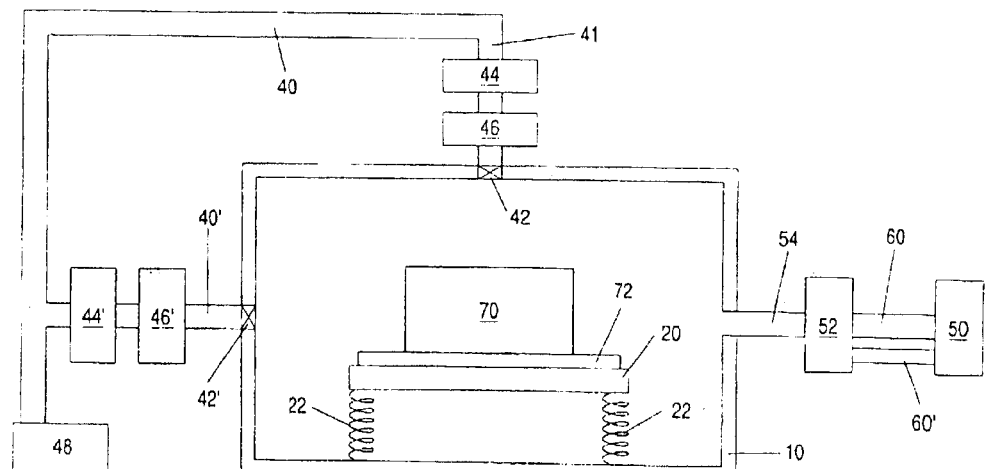

US 5,942,699 C1

Figure 1:
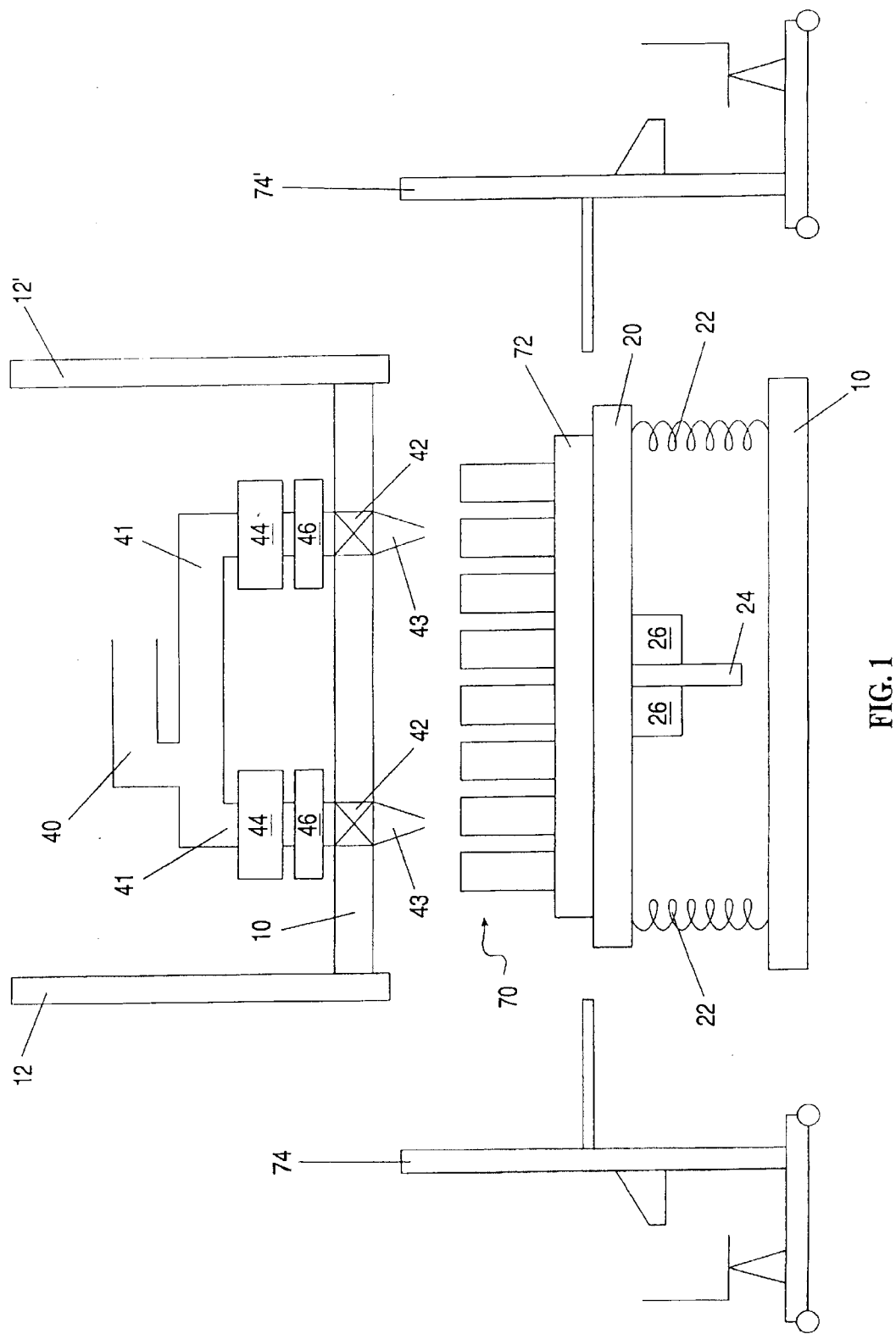
Figure 2:
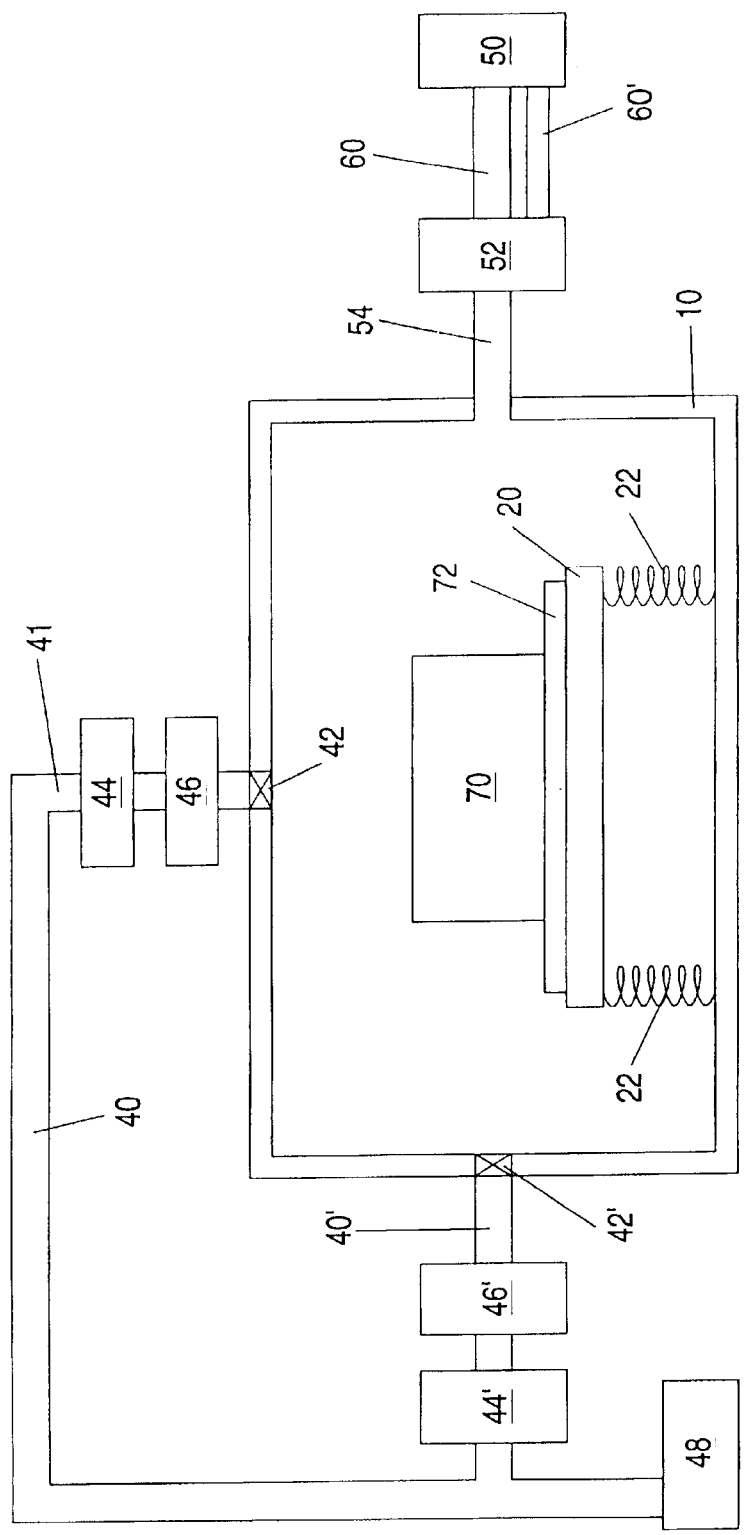
Figure 3:
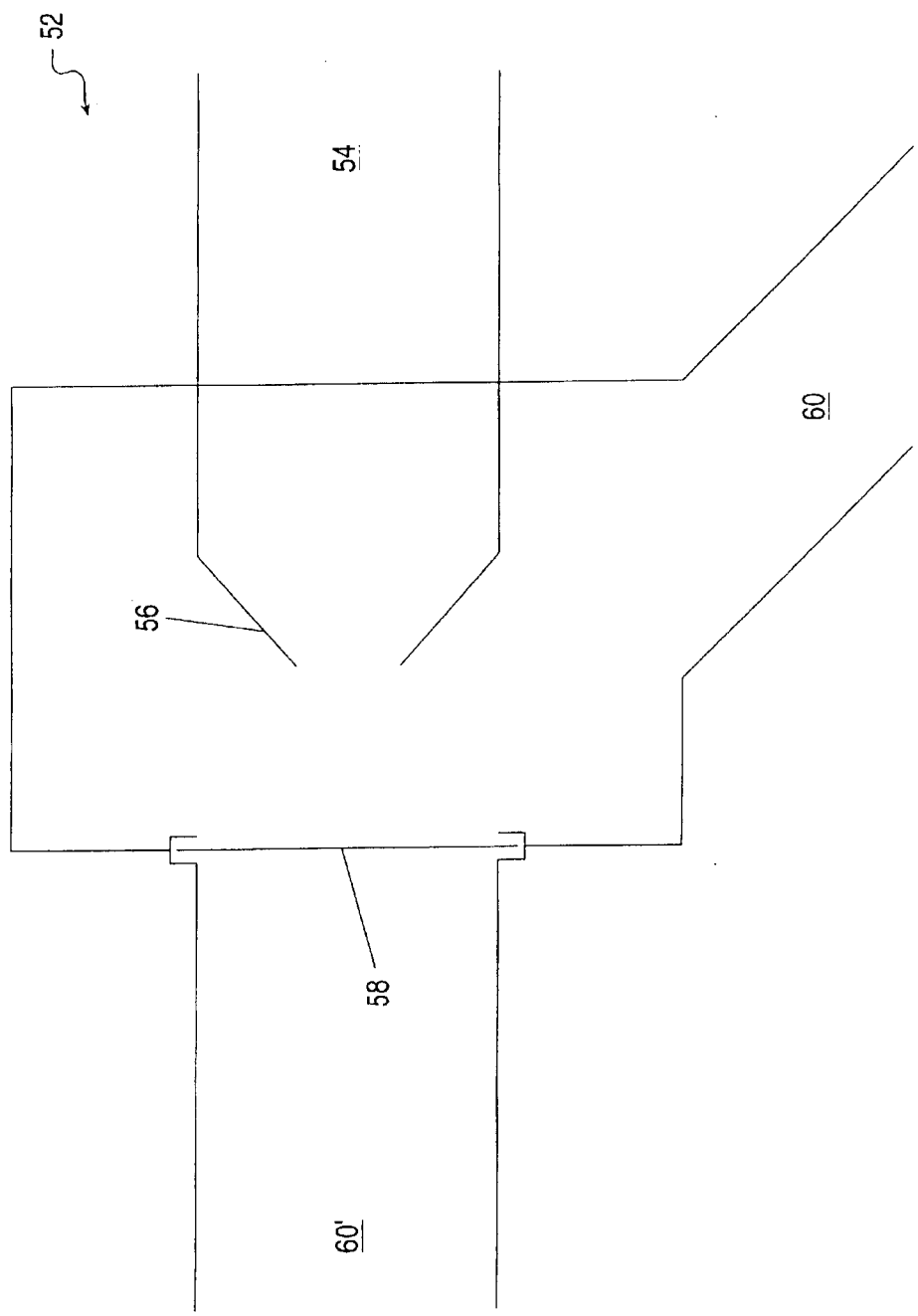

EX PARTE
REEXAMINATION CERTIFICATE
ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 10–18, 21 and 25 is confirmed.

Claims 1–9, 19 and 26–27 are cancelled.

Claims 20 and 22–23 are determined to be patentable as amended.

Claim 24, dependent on an amended claim, is determined to be patentable.

New claims 28–36 are added and determined to be patentable.

20. The method of claim [19] *28*, wherein said solvent is selected from the group consisting of carbon dioxide, acetone, dimethyl sulfoxide, propanol and organic amides.

22. An apparatus for sampling cargo for particulates and vapors of chemical residues, comprising:
(a) a chamber, enclosing a gas at a certain pressure, wherein the cargo is [placed] *sealed* for sampling;
(b) a mechanism for heating a portion of said gas and introducing said heated gas into said chamber in bursts, thereby releasing the particulates and vapors into said gas;
(c) a collection system for removing the particulates and vapors from said gas; and
(d) a mechanism for inducing a flow of said gas, together with said particulates and vapors, towards said collection system.

23. An apparatus for sampling cargo for particulates and vapors of chemical residues, comprising:
(a) a chamber, enclosing a gas at a certain pressure, wherein the cargo is [placed] *sealed* for sampling;
(b) a mechanism for directing jets of said gas at the cargo, thereby releasing the particulates and vapors into said gas;
(c) a collection system for removing the particulates and vapors from said gas; and
(d) a mechanism for inducing a flow of said gas, together with said particulates and vapors, towards said collection system.

*28. A method for sampling surfaces and interiors of a plurality of items for contaminant particulates and contaminant vapors, comprising the steps of:*
*(a) sealing the items inside a chamber containing air;*
*(b) introducing a solvent to said air;*
*(c) agitating the items by directing jets of said air at the items, thereby releasing the particulates and the vapors from the surfaces and the interiors of the items into said air;*
*(d) inducing a flow of said air, together with the released particulates and vapors, towards a collection system.*

*29. The method of claim 14, wherein said chamber is substantially airtight.*

*30. The method of claim 17, wherein said chamber is substantially airtight.*

*31. The apparatus of claim 22, wherein said chamber is substantially airtight.*

*32. The apparatus of claim 23, wherein said chamber is substantially airtight.*

*33. The method of claim 29, wherein said chamber is sufficiently airtight for a pressure of said air to be cycled between about 1.5 atmospheres and about 0.5 atmospheres.*

*34. The method of claim 30, wherein said chamber is sufficiently airtight for a pressure of said air to be cycled between about 1.5 atmospheres and about 0.5 atmospheres.*

*35. The apparatus of claim 31, wherein said chamber is sufficiently airtight for said pressure of said gas to be cycled between about 1.5 atmospheres and about 0.5 atmospheres.*

*36. The apparatus of claim 32, wherein said chamber is sufficiently airtight for said pressure of said gas to be cycled between about 1.5 atmospheres and about 0.5 atmospheres.*

* * * * *